(12) United States Patent
Auranen et al.

(10) Patent No.: US 9,201,029 B2
(45) Date of Patent: Dec. 1, 2015

(54) METHOD FOR DETERMINING THE ORE CONTENT OF DRILL CUTTINGS

(75) Inventors: Ilpo Auranen, Espoo (FI); Jukka Raatikainen, Espoo (FI)

(73) Assignee: ATLAS COPCO ROCK DRILLS AB, Orebro (SE)

( * ) Notice: Subject to any disclaimer, the term of this patent is extended or adjusted under 35 U.S.C. 154(b) by 449 days.

(21) Appl. No.: 13/384,029

(22) PCT Filed: Jul. 16, 2010

(86) PCT No.: PCT/FI2010/050601
§ 371 (c)(1),
(2), (4) Date: Apr. 6, 2012

(87) PCT Pub. No.: WO2011/007053
PCT Pub. Date: Jan. 20, 2011

(65) Prior Publication Data
US 2012/0187286 A1    Jul. 26, 2012

(30) Foreign Application Priority Data

Jul. 17, 2009    (FI) ..................................... 20095797

(51) Int. Cl.
*G01N 23/22*     (2006.01)
*G01N 23/223*    (2006.01)
*G01N 33/24*     (2006.01)

(52) U.S. Cl.
CPC .............. *G01N 23/223* (2013.01); *G01N 33/24* (2013.01); *G01N 2223/076* (2013.01)

(58) Field of Classification Search
CPC . G01N 23/223; G01N 223/076; G01N 33/24; G01N 33/241

USPC ............ 250/573, 428, 432 R, 433, 435, 436, 250/461.1, 255, 301
See application file for complete search history.

(56) References Cited

U.S. PATENT DOCUMENTS 2,367,664 A  *  1/1945  Campbell et al. ............... 436/30
4,134,012 A     1/1979  Smallbone et al.
(Continued)

FOREIGN PATENT DOCUMENTS

CA    2071089 A1    12/1993
EP    0 426 231 A2    5/1991
(Continued)

OTHER PUBLICATIONS

Jenkins et al., *Quantitative X-ray Spectrometry*, 1995, 2nd Ed., pp. 6-39, New York, Marcel Dekker, Inc.
(Continued)

*Primary Examiner* — Yara B Green
(74) *Attorney, Agent, or Firm* — Oliff PLC

(57) ABSTRACT

The object of this invention is a method for determining ore contents of drill cuttings by irradiating and by detecting fluorescence radiation and scattering radiation. According to the method, drill cuttings being essentially immediately retrieved from the drill hole is arranged as a layer, the upper surface of which is at least partly free from water, a statistically sufficiently representative defined area of the layer is irradiated and the fluorescence of the irradiation is measured for element-characteristic intensities and for Compton-scattering or coherent scattering intensities. The element-characteristic intensities are corrected using coefficients empirically defined from Compton-scattering and/or coherent scattering in order to compensate for the damping due to the coverage effect of water.

5 Claims, 5 Drawing Sheets

(56) References Cited

U.S. PATENT DOCUMENTS

Figure 1:
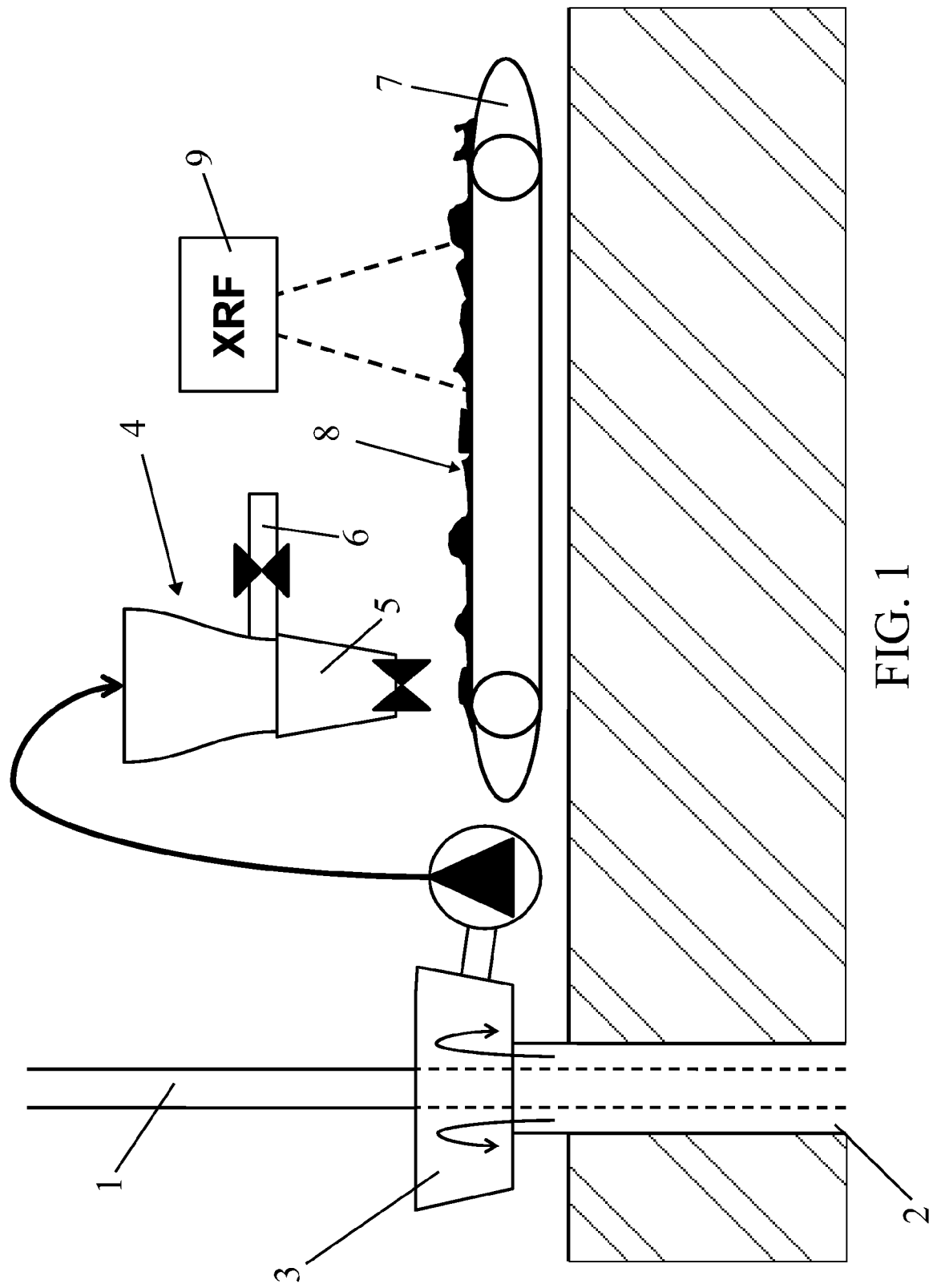

| | | | |
|---|---|---|---|
| 4,609,821 A * | 9/1986 | Summers | 250/255 |
| 5,110,457 A | 5/1992 | Krawl et al. | |
| 5,269,906 A * | 12/1993 | Reynolds et al. | 208/13 |
| 5,461,654 A | 10/1995 | Grodzins et al. | |
| 5,519,214 A * | 5/1996 | Houwen et al. | 250/256 |
| 6,386,026 B1 | 5/2002 | Zamfes | |
| 2003/0056581 A1 * | 3/2003 | Turner et al. | 73/152.19 |

FOREIGN PATENT DOCUMENTS

| | | |
|---|---|---|
| FI | 120164 B | 7/2009 |
| SU | 754 274 A1 | 8/1980 |
| WO | 93/17326 A1 | 9/1993 |
| WO | WO 2009/101265 A1 | 8/2009 |

OTHER PUBLICATIONS

Sokolov et al., "On-line analysis of chrome-iron ores on a conveyor belt using x-ray fluorescence analysis," *X-Ray Spectrometry*, 2005, pp. 456-459, vol. 34, John Wiley & Sons, Ltd.

Potts et al., "Atomic spectrometry update. X-Ray fluorescence spectrometry," *J. Anal. At. Spectrom.*, 2005, pp. 1124-1154, vol. 20, The Royal Society of Chemistry.

Nienhaus et al., "Dilution control of Run-of-mine ore with an innovative on-line technique, Application of laser-induced fluorescence (LIF) in the mining industry," <http://www.imr.rwth-aachen.de/downloads/200309australiansminingmonthly.pdf>.

Australian Patent Examination Report issued in Australian Patent Application No. 2010272466 dated Jun. 27, 2013.

Finnish Search Report issued in Finnish Patent Application No. 20095797 dated Apr. 28, 2010 (w/ partial translation).

International Search Report issued in International Patent Application No. PCT/FI2010/050601 dated Dec. 14, 2010.

Written Opinion of the Itnernational Searching Authority issued in International Patent Application No. PCT/FI2010/050601 dated Dec. 14, 2010.

Sep. 24, 2014 Supplementary European Search Report issued in European Application No. 10799483.

Y. Imanishi et al., "Experimental Parameters for XRF Analysis of Soils," Jan. 1, 2010.

M.A. Phedorin, et al., "Prediction of absolute concentrations of elements from SR XRF scan measurements of natural wet sediments," Nuclear Instruments & Methods in Physics Research, vol. 543, No. 1 (2005) pp. 274-279.

R. Tjallingii, et al., "Influence of the water content on X-ray fluorescence core-scanning measurements in soft marine sediments," Geochemistry, Geophysics, Geosystems, vol. 8, No. 2, (2007) 12 pages.

* cited by examiner

FIG: 4A

METHOD FOR DETERMINING THE ORE CONTENT OF DRILL CUTTINGS

This invention relates to a method for analyzing drill cuttings according to an on-line principle.

The separate material and drill dust known as drill cuttings formed at ore mines during the drilling of blast holes and sample holes is usually dry when drilled at the surface. In such case, the drill rig comprises means to blow the drill cuttings out of the drill hole using compressed air, collecting the drill cuttings and conveying it to the proximity of the drill rig. Samples are also collected from the drill cuttings formed this way, which samples are, according to known methods, used to determine an average ore content of the whole depth of the drill hole.

When drilling below the ground surface, formed drill cuttings have to be absorbed into water in order not to dust the air in the mine galleries, for example. This is usually done by implementing the flushing of the drill holes using water instead of air, and as a result the drill cuttings exiting the drill hole are very wet and sludge-like. Wet drill cuttings are also formed in surface drilling when drilled deeper than the water table.

The problem of analyzing wet drill cuttings is their water content, which greatly disturbs and in most cases prevents analyzing wet drill cuttings. This is because in effect samples cannot be taken from wet drill cuttings, since when exiting a drill hole it does not form a pile but spreads to form an even layer in the near vicinity due to its sludge-like composition. If such wet drill cuttings are collected to form a sample, for example in a bucket, the analysis poses a problem as the water contents of the sample prevents the use of traditional real time analyzing methods, since the material to be analyzed is mixed with water and the analyzing methods of traditional analyzing devices are not able to penetrate water.

The sludge density of wet drill cuttings in mining operations is typically 5-10 percent solids by weight. Drill cuttings are used to identify ore layers by taking drill cuttings samples and analyzing them in a laboratory. However, laboratory measurements are too time-consuming for the purpose of controlling the drilling, that is to say to optimize the length of drill holes from the viewpoint of blasting to track ore limits.

Measuring drill cuttings using known methods directly from the sludge, for example with a design using a sludge cuvette, causes a great error in the analysis due to low water content and large grain size fractions of drill cuttings.

A possible solution is to measure the cuttings after filtration, for example directly from a filter belt. Using filtration methods in a mine environment in connection with drilling or directly mounted to the drill is nevertheless complex and the devices used require a lot of maintenance.

A solution according to the present invention offers a method for analyzing drill cuttings, including drill cuttings in a sludge state, in real time according to the on-line principle. The method according to the invention is generally suitable for direct measuring of drill cuttings samples, particularly from wet drill cuttings. The on-line principle or method in this context means that drill cuttings are analyzed as they are formed, as soon as possible after being formed and flushed out of the drill hole, in which case the results of the analysis are quickly available. In a solution according to the invention, the time span for the analysis of drill cuttings is approximately 5-60 seconds, during which the drill cuttings conducted through the assay device is analyzed.

In the method according to the invention, care is taken that the drill cuttings due for assay form a layer, the upper surface of which is at least partly free of water. If the analysis is carried out on drill cuttings sludge, it usually requires that the sludge is thickened prior to the assay. In the assay, a defined area representing a statistically sufficient sample of the composition of the drill cuttings is irradiated. Element-specific intensities and the intensity of Compton-scattering, or alternatively the intensity of coherent scattering or both are measured from the fluorescence of the irradiation. Coefficients for compensating for the dampening effect to element-specific intensities due to free water coverage in the measuring area are determined from the scattering intensities. The coefficients are based on experimental measurements.

Figure 2:
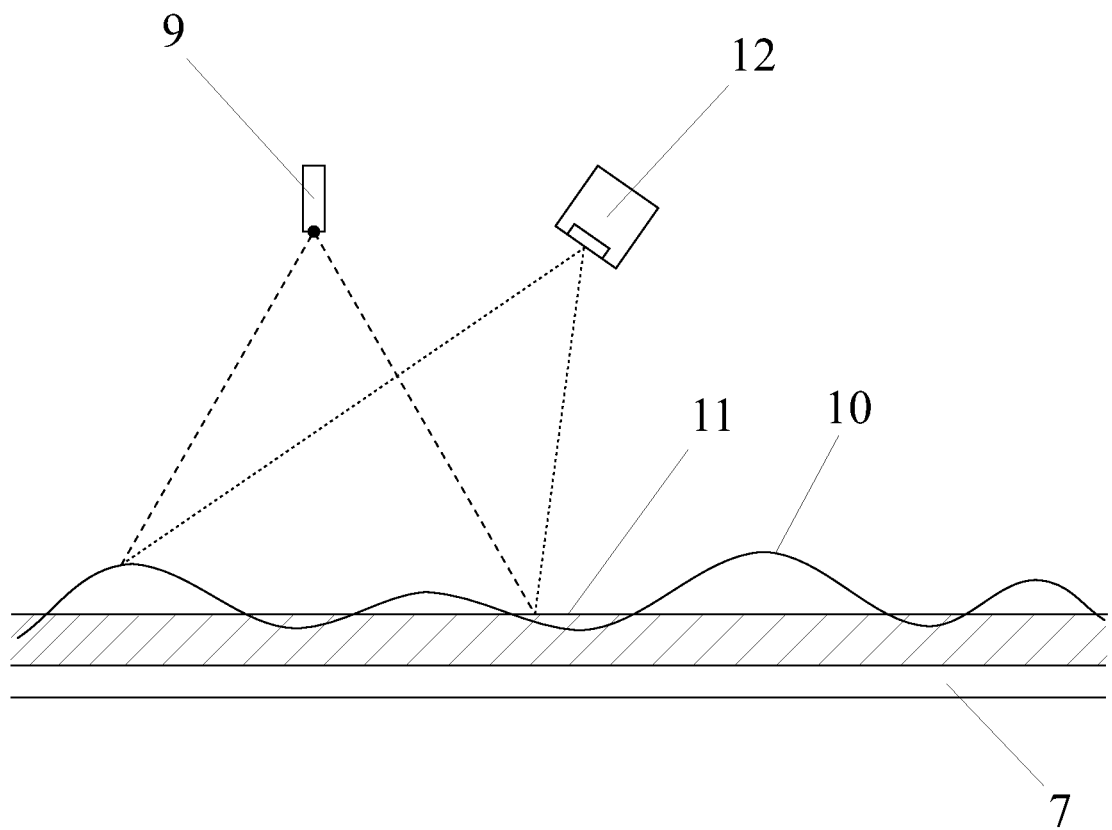
Figure 3A:
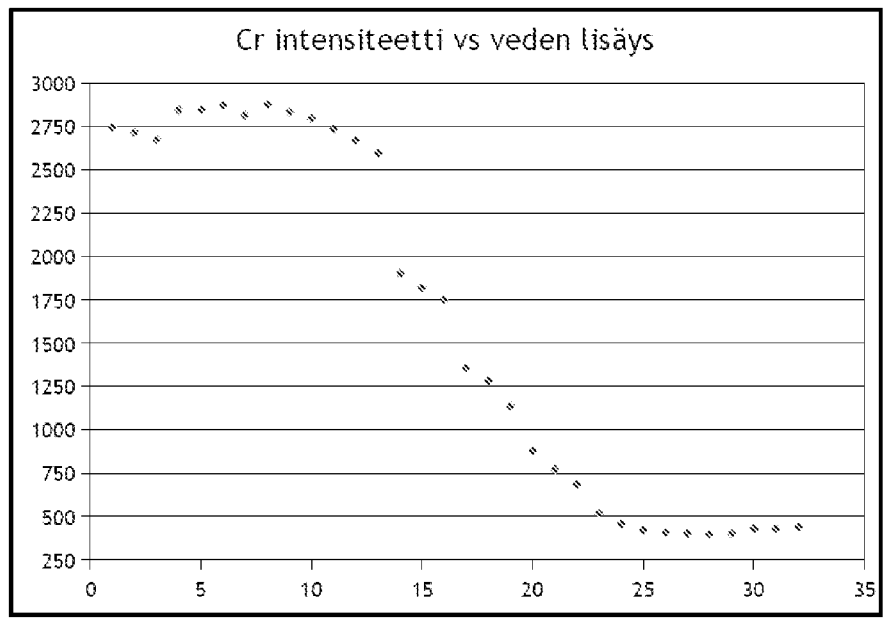
Figure 3B:
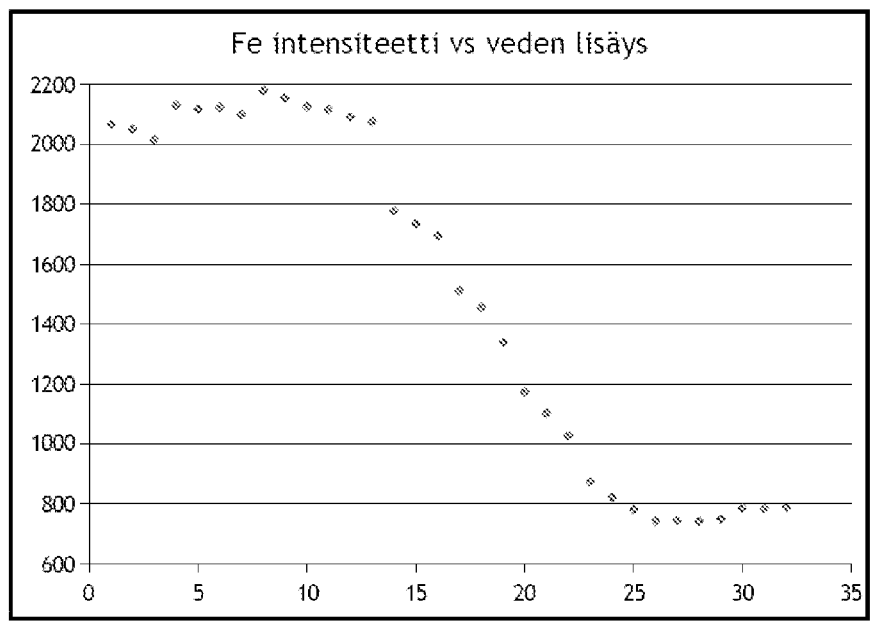
Figure 4B:
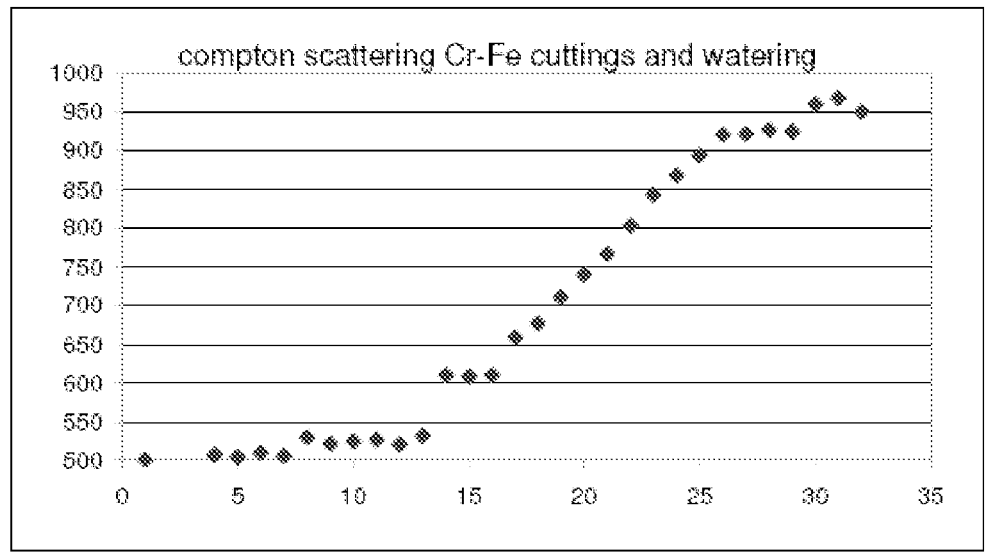
Figure 4B:
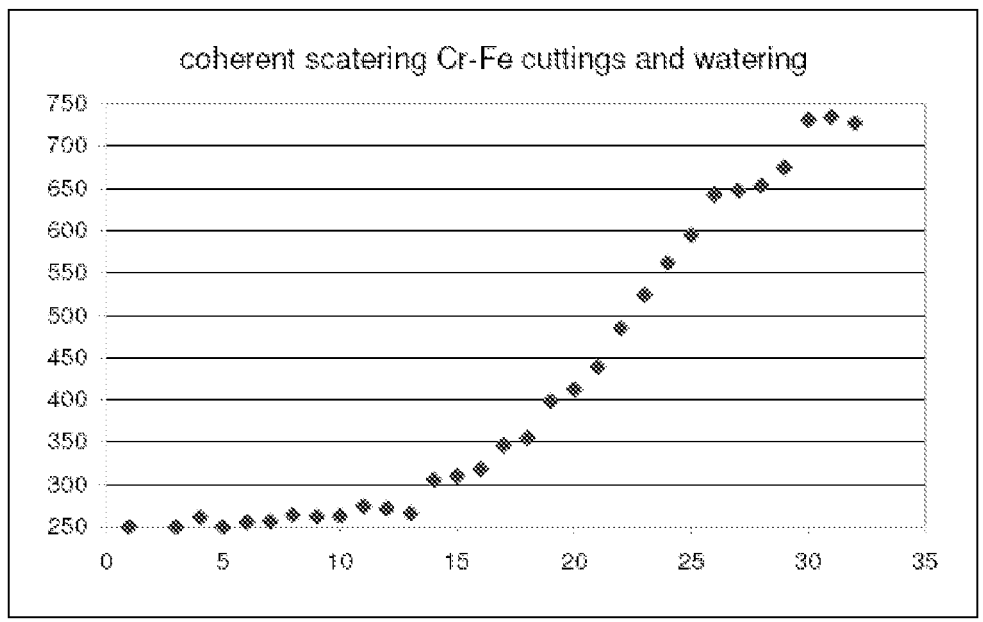
Figure 5A:
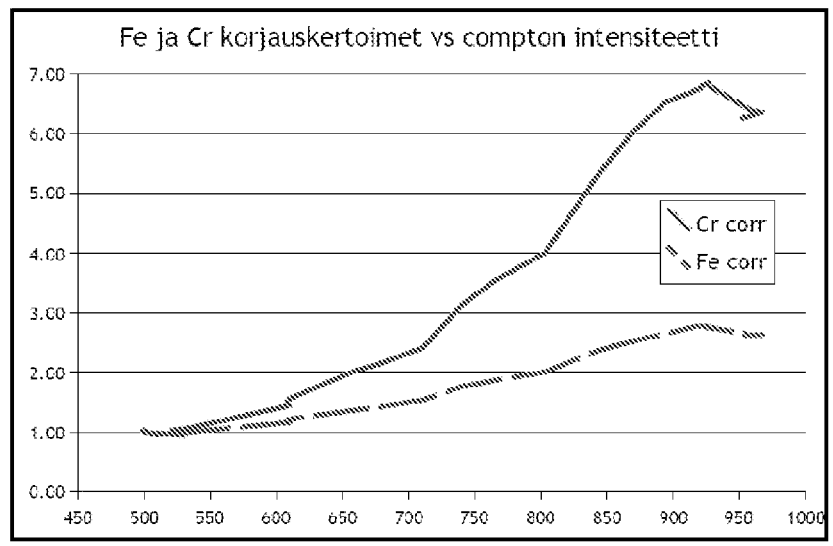
Figure 5B:
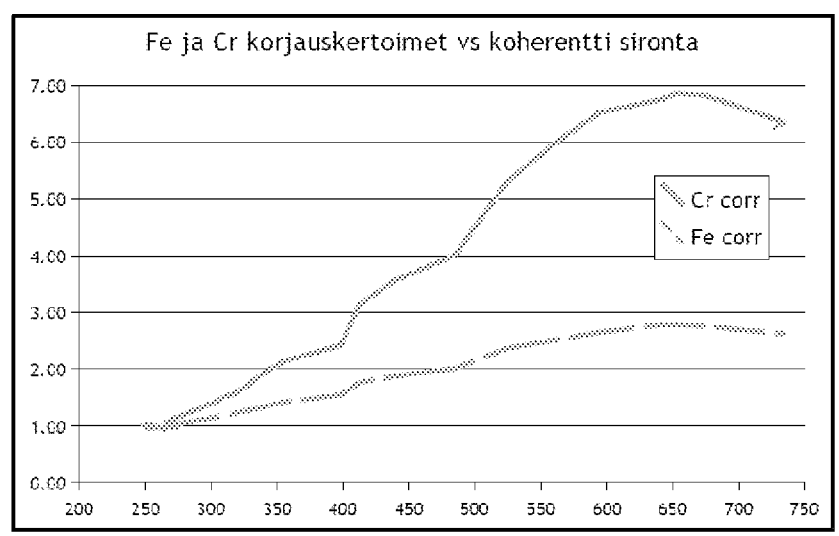

Next, the invention and its various embodiments are described in more detail as examples given below and referring to the enclosed figures, in which FIG. 1 illustrates schematically a device for collecting drill cuttings and for forming an ore sample for assay according to the invention, FIG. 2 illustrates schematically a solution for a method for analyzing an ore sample according to the invention, FIG. 3A illustrates changes in the XRF-radiation intensity of a chromium sample as the water content of the sample increases, FIG. 3B illustrates changes in the XRF-radiation intensity of an iron sample as the water content of the sample increases, FIG. 4A illustrates changes in the Compton-scattering of a sample containing chromium and iron as the water content of the sample increases, FIG. 4B illustrates changes in the coherent scattering of a sample containing chromium and iron as the water content of the sample increases, FIG. 5A illustrates correction coefficients for iron and chromium relative to Compton-scattering, and FIG. 5B illustrates correction coefficients for iron and chromium relative to coherent scattering.

FIG. 1 illustrates an apparatus according to the invention for forming an ore sample from wet drill cuttings when drilling on the surface. In the situation schematically illustrated in the figure, a hole 2 is being drilled in the bedrock with a drill 1 of a drill rig, the hole advantageously being a blast hole. When drilling, wet sludge-like drill cuttings gush out of the drill hole 2 due to the flushing of hole 2, which flushing is carried out by means (not shown) integrated with the drill rig.

Drill cuttings gushing out from the drill hole is recovered using a known technique such as a collar 3, from which it is introduced to a settler 4 functioning as a thickening apparatus. The settler is of a conventional structure having a conical lower part 5, and an overflow 6 for the removal of liquid released from the solids. In the lower part 5 of the thickener, the solids can further be mixed in order to eliminate harmful interference caused by fractionation, which could cause distortion in the assays.

Drill cuttings are discharged from the lower part of the settler 5 through a valve or for example a rotary vane feeder to a conveyor 7, to which has been adapted an assay device for use in implementing the invention. Conveyor 7 can be an ordinary circulating belt conveyor, onto which drill cuttings introduced from the settler spread, forming a layer which is representative for the purpose of assay.

In order to form a suitable layer on the conveyor 7, the conveyor can be formed as a chute and possibly the belt of the conveyor is also permeable. A prerequisite for the layer 8 is that at least a part of its top surface is free from water as the layer enters the area of influence of the assay device. This state is preferably to be established in a thickening step prior to the conveyor, such as the settler 4 or an equivalent apparatus (e.g. a hydrocyclone) suitable for dewatering solids-containing sludge. On the other hand, drill cuttings flushed from drill hole 2 can already contain enough solids (when flushing with air) in which case it can be conducted directly onto the conveyor 7 for ore content assay.

If analysis of the fine-grained material mixed with water is also desired, the water discharged from separator 4 can be conducted through a filter which collects the fine-grained material and separates it from the water, thus enabling analysis of the fine-grained material.

FIG. 2 illustrates schematically an analysis design based on the XRF method for the analysis of drill cuttings. FIG. 7 illustrates the assay of drill cuttings located on the conveyor 7, which drill cuttings comprise a solid phase 10 and a water phase 11. In the example of the figure, the water phase has been removed from the drill cuttings to the extent that the solid phase at least partly transgresses the upper surface of the water phase.

A water phase is largely disadvantageous for the X-ray fluorescence (XRF) method, because water occasionally completely absorbs the characteristic XRF radiation formed below it and partly prevents the identification of elements and quantitative analysis.

In the embodiment illustrated in FIG. 2, the analysis of wet drill cuttings is carried out by irradiating it with X-ray source 9, the beam of which advantageously forms, for example, a rectangular assay zone on the conveyor. The radiation reflected from the assay zone is observed using radiation detector 12. Radiation detector 12 detects element-specific radiation quanta and scattered radiation quanta from the area radiated, i.e. excited by the radiation beam of X-ray source 9. Scattering can be determined as Compton scattering or coherent scattering or both.

The utilization of scattering in this method is based on the fact that with the selected exciting radiation, water advantageously causes considerably—even several times—greater scattering when compared to the scattering caused by rock material or metal ore material. The intensity of scattering thus grows as the amount of water increases and covers the surface of the sample being measured, and correspondingly the intensity of characteristic XRF X-ray radiation dampens as water covers the rock material of the drill cuttings being analyzed. Therefore, the scattering provides information of the portion covered by water of the area being evaluated, and on the basis of this information, coefficients for measured values of the observed element-specific fluorescence values can be obtained from empirical measurements, taking into account the dampening caused by water in the said measured values.

The irradiated area should be extensive enough in order to obtain a reliable sample of the drill cuttings being analyzed. The size of the area must be such that the number of grains being measured is sufficiently representative with respect to sampling theory. For example, as the largest grains in a drill cuttings sample can be up to 10 mm in diameter and preferably there should be hundreds of them in the area being measured, the area to be measured should be selected to be an order of magnitude larger (e.g. 10×10 cm). The sample should also be spread over a larger area, which area is measured i.e. scanned as comprehensively as possible in one way or another.

In the example of FIG. 2, the radiation detector 12 and the radiation source 9 are located at a constant distance from the wet drill cuttings being analyzed. In a solution according to the invention, the sample to be analyzed and the surface of the water phase can also be at a varying distance from the radiation detector and the radiation source, but in this case a correction factor has to be added to compensate the effects of distance variation, correcting the intensities of both scattering and element-characteristic radiation. The distance of the radiation detector and the radiation source from the sample to be analyzed can be measured by a known method, such as laser measurement.

The evaluation of thickened drill cuttings can be done during a stage when drilling is suspended as drill rods are added and extended, and when the drilling continues, the following sample to be evaluated is collected in the settler 4.

The following describes an example of a method for analysis according to the invention in order to determine compensation coefficients for the effects of water. Being analyzed are ordinary drill cuttings with water added in such a way that the drill cuttings' moisture content first grows rapidly, and finally the cuttings start to get partially and fully covered with water. The measuring method used is XRF measurement. The analyzed drill cuttings sample contained chromium-iron ore.

In this experiment, the X-ray beam exciting the XRF is considerably larger than grain size, i.e. the measurement has been taken from a relatively large area (grain size from 0.1 to 10 mm and beam 100×100 mm). The radiation detector measured not only the elements' XRF intensities but also particularly the wavelength and intensities of Compton scattering and coherent scattering.

FIGS. 3A and 3B illustrate the decrease of XRF-radiation intensities of the elements chromium (FIG. 3A) and iron (FIG. 3B). It can be seen from the figures that the intensity of XRF-radiation (y-axis) decreases slowly at first as the sample is moistened in stages (x-axis) number 1 to 13. Finally, the sample is initially partially covered and finally fully submerged with the number of moistening stages (x-axis) 14 to 25. When the entire sample is submerged, the new moistening stages 26-32 no longer affect the intensities.

FIGS. 4A and 4B in turn, show how the Compton (FIG. 4A) and coherent (FIG. 4B) scattering in turn increase when the amount of water increases, as water acts as a cause of scattering differing from that of ore. Especially in a situation where the water actually begins to cover the drill cuttings, the amount of scattering grows vigorously. In a solution according to the invention, when measuring the chromium and iron content using the XRF intensities of these elements in such a situation, an empirical correction is done. The correction is based on the decrease in intensity illustrated in FIGS. 3A and 3B and on the corresponding increase, shown in FIGS. 4A and 4B, in scattering intensity as the amount of water increases.

In the example the dampening and/or change of the intensities of iron and chromium is mathematically corrected using the values of correspondingly measured scattering intensities. A simple empirical compensation factor can be calculated using the ratio of the original dry drill cuttings' iron or chromium intensity to the observed (measured from a moist or wet sample) intensity. The corresponding absolute scattering intensities in FIGS. 4A and 4B determine correction factors in FIGS. 5A and 5B for iron and chromium intensities.

A simple correction coefficient which may be used is consequently the ratio between measured intensities of a dry and a wet sample, the value of which can be looked up at the point of the measured value of Compton or coherent scattering intensity in the empirically obtained charts in FIG. 5A or 5B.

In a more sophisticated model, for example a polynomial function is fitted to the previous measurement results, providing a more accurate value for the compensation factor than previously. Also, a mathematical model of the combination of two previous scatterings can be used for calculating a more accurate and reliable value for the coefficient.

A measuring method based on XRF is suitable for measuring element content in wet drill cuttings. In a solution according to the invention, an ultraviolet radiation emitting laser may also advantageously be used according to the LIF-method (LIF, Laser Induced Fluorescence) when the measurement of mineral contents in wet drill cuttings is desired. In the LIF method, when analyzing samples using a wide laser beam, certain minerals become excited and emit afterglow, i.e. fluorescence. The wavelength and the rate of fading of this afterglow permit the identification of the desired minerals. LIF's advantage is the penetration into water of UV radiation, which penetration is significantly higher than that of ordinary light.

In a solution according to the invention it is also advantageously possible to associate positioning information from the progression of the drilling with the collected drill cuttings sample.

In a solution according to the invention, the sample collector may be a separate unit or it could be a fixed unit of the drill rig or the assay device.

The invention claimed is:

1. A method for determining the ore content of drill cuttings, comprising:
    irradiating the drill cuttings with X-ray radiation and detecting fluorescence radiation and scattering radiation from the drill cuttings, the drill cuttings having been essentially immediately recovered from a drill hole and arranged as a layer, an upper surface of which is partly free from water, a solid phase of the layer partly transgressing an upper surface of a water phase of the layer,
    defining and irradiating a statistically sufficiently representative area of the layer, and
    measuring the fluorescence of the irradiation for element-characteristic intensities occurring in the ore, and for Compton-scattering and/or coherent scattering intensities,
    wherein the element-characteristic intensities are corrected using coefficients empirically derived from Compton-scattering and/or coherent scattering in order to compensate for damping due to a coverage effect of water.

2. The method according to claim 1, wherein the drill cuttings are subjected to dewatering prior the determination.

3. The method according to claim 2, wherein dewatering is carried out by solids settling.

4. The method according to claim 3, wherein the settled solids are introduced at a measurement point in a mixed and unclassified state.

5. The method according to claim 1, wherein an essentially mixed and homogenized layer of drill cuttings is set into an advancing motion during the implementing of the determination, in order to ensure the measurement being statistically representative.

* * * * *